United States Patent
Scarasso et al.

(10) Patent No.: US 10,255,622 B2
(45) Date of Patent: Apr. 9, 2019

(54) STATISTICAL FINANCIAL SYSTEM AND METHOD TO VALUE PATIENT VISITS TO HEALTHCARE PROVIDER ORGANIZATIONS FOR FOLLOW UP PRIORITIZATION

(71) Applicant: Continuum Health Technologies Corp., Austin, TX (US)

(72) Inventors: Albert Scarasso, Austin, TX (US); Aquiles Mata, Austin, TX (US); Michael Craig Tulkoff, Austin, TX (US)

(73) Assignee: CONTINUUM HEALTH TECHNOLOGIES CORP., Austin, TX (US)

( * ) Notice: Subject to any disclaimer, the term of this patent is extended or adjusted under 35 U.S.C. 154(b) by 0 days.

(21) Appl. No.: 13/665,032

(22) Filed: Oct. 31, 2012

(65) Prior Publication Data
US 2014/0122098 A1 May 1, 2014

(51) Int. Cl.
*G16H 40/00* (2018.01)
*G06Q 30/02* (2012.01)
(Continued)

(52) U.S. Cl.
CPC ......... *G06Q 30/0278* (2013.01); *G06F 19/00* (2013.01); *G06Q 10/0631* (2013.01); *G06Q 50/22* (2013.01); *G16H 40/00* (2018.01)

(58) Field of Classification Search
CPC .... G06Q 50/22; G06Q 50/24; G06Q 30/0278; G06F 19/328; G16H 40/00
See application file for complete search history.

(56) References Cited

U.S. PATENT DOCUMENTS

2003/0065534 A1* 4/2003 McCartney ................ 705/2
2009/0048877 A1* 2/2009 Binns .................. G06F 19/328
705/4

(Continued)

OTHER PUBLICATIONS

Silver et al., Case Study: How to Apply Data Mining Techniques in a Healthcare Data Warehouse, Summer 2001, Journal of Healthcare Information Management, vol. 15, No. 2, pp. 155-164. (Year: 2001).*

*Primary Examiner* — Christopher L Gilligan
(74) *Attorney, Agent, or Firm* — Workman Nydegger (57) ABSTRACT

A Statistical financial system to value patient visits to healthcare providers allows healthcare providers to optimize their financial outcomes when billing insurance payers for services rendered in the course of patient visits. Commercial healthcare information systems today lack the ability to value these services in advance. Given the complexity of valuing services based on many variables and resource limitations, a predictive valuation provides the user with the information for accurate and timely decision making. Using the historical data, the system creates a predictive model of future claims by creating attribute patterns from the data. As new information comes into the system, these attribute patterns are compared to the real-time data in order to create a value for a service and an overall visit. Using the valuation, the system will now be able to prioritize all follow-up tasks. The overall result is a better financial performance for the healthcare provider.

20 Claims, 4 Drawing Sheets

(51) Int. Cl.
  *G06F 19/00* (2018.01)
  *G06Q 10/06* (2012.01)
  *G06Q 50/22* (2018.01)

(56) References Cited

U.S. PATENT DOCUMENTS

2009/0299768 A1* 12/2009 Petrasich et al. ................ 705/3
2010/0114599 A1*  5/2010 Lanning et al. .................. 705/2
2010/0312581 A1* 12/2010 Wachtell et al. ................. 705/3

* cited by examiner

STATISTICAL FINANCIAL SYSTEM AND METHOD TO VALUE PATIENT VISITS TO HEALTHCARE PROVIDER ORGANIZATIONS FOR FOLLOW UP PRIORITIZATION

FIELD OF THE INVENTION

This invention relates in general to statistical financial system and method to value patient visits to healthcare provider organizations for follow up prioritization, and more particularly, to methods and systems of providing valuation of healthcare provider services and visits in the future or present within the context of a healthcare analytical system using historical statistical methods and the utilization of the valuation for work prioritization.

BACKGROUND OF THE INVENTION

The nature of healthcare businesses requires that healthcare organizations perform a financial clearance prior to or when the patient arrives at their facilities for their services. The amount of work and tasks associated with each healthcare organization's service can easily surpass the number of resources available to properly address all the follow up tasks and issues. When issues or notifications are not addressed in a timely manner, it could result in the reduction or rejection of payment for the service, thus impacting the financial outcome for the organization. There are different ways that organizations could prioritize the work based on the type of service or procedure or the amount charged for the service. However, because of the nature of the healthcare business, the true monetary value of a service can vary widely depending upon the type of payer, the patient or subscriber's employer, and the location where the services are being delivered. Different payers' contractual rules result in different values for the same services. In most cases, the type and nature of a healthcare visit makes it very difficult to properly identify and value all of the services associated with a healthcare visit.

Moreover, currently available healthcare scheduling, registration, and other healthcare information systems do not provide a way to manage and prioritize and resolve activities and based on a monetary value of the services for a patient visit to a healthcare provider prior to the point in time that such services are rendered. This system provides a predictive valuation for the provided services prior to the performance of those services.

Thus, there is a need for Statistical financial system and method to value patient visits to healthcare provider organizations for follow up prioritization. Healthcare provider organizations have a critical financial need to identify problems with patient registrations and correct those problems in a timely fashion in order to prevent denials and rejections by the insurance company payers. Given time and resource constraints, it is important to not only identify the correct issues, but to prioritize and track those issues. A prioritization must be based on financial impact and the valuation of the visit based on services is an important feature. Again, given the time and resource constrains involved, having a predictive method to assign a value to services before they are rendered based on statistical methods, and thus creating a value for the patient visit is a unique and innovative solution.

SUMMARY OF THE INVENTION

A statistical financial system and method to value patient visits to healthcare provider organizations for follow up prioritization will allow healthcare providers to optimize their financial outcomes when billing insurance payers for services rendered in the course of patient visits to said providers. Commercial healthcare information systems today lack the ability to value these services in advance and put the healthcare provider at a tactical disadvantage. Given the full complexity of valuing services based on many variables such as the insurance contract, geographic location, physician, etc., as well as a limitation in both time and resources, a predictive valuation provides the healthcare provider user with a huge advantage with the information necessary for accurate and timely decision making A statistical database is created based on historical healthcare claims information. Using the historical data, the system creates a predictive model of future claims by creating attribute patterns from the data. As new information comes into the system in the way of patient registrations, these attribute patterns are compared to the real-time data in order to create a value for a service and an overall visit. By having a valuation and a set of business exceptions in the form of a user alert, the system will be able to prioritize how follow-up tasks should be worked and can perform valuable decision support for the user, who can focus on the actual tasks to perform. The overall result is a better financial performance for the healthcare provider.

In one set of embodiments, a method to utilize a statistical database that combines the data from bills submitted by the healthcare organizations to the different healthcare payers, the healthcare payers' detailed explanation of payments for each service and detailed data for the patient visit to create template of attribute patterns for future predictions.

In another set of embodiments, the historically-generated attribute patterns are matched with attribute patterns from new visits to establish an estimated monetary value for the new visits. Once a patient visit to a healthcare provider is assigned a monetary value, the system associates such a monetary value to other business rules to create a value processing weight for the financial clearance for decision making, prioritization of follow up tasks and issues.

In still another set of embodiments, a method for using the valuation of the listed services for the visit in order to value the overall visit, expose related issues to the provider organization, and provide a prioritization of issues based on a monetary value.

In other similar embodiments a method to continuously monitor the identified and prioritized tasks and issues to resolution in order to maximize financial outcome.

While the specified embodiments are unique, they will exist within a system defined by prior art in a commercial healthcare software solution entitled Revenue Orchestrator from DaVincian Technologies, which has existed in various releases since 2003. The technology to detect issues based on knowledge rules and provide an alert to a user is prior art of DaVincian Technologies.

The foregoing general description and the following detailed description are exemplary and explanatory only and are not restrictive of the invention, as defined in the appended claims.

BRIEF DESCRIPTION OF THE DRAWINGS

The drawings accompanying and forming part of this specification are included to depict certain aspects of the specified system and method. The present system and method is illustrated by way of example and not limitation in the accompanying figures. It should be noted that elements in the figures are illustrated for simplicity and clarity and have not necessarily been drawn to scale.

DETAILED DESCRIPTION OF THE PREFERRED EMBODIMENTS

A few terms are defined here to aid in the understanding of the descriptions and drawings that follow.

The term "healthcare provider" or simply "provider" represents the entity that provides medical care to a patient in return for some fee, which may be billed to an insurance company, the patient, the patient's guarantor, or some combination. The provider may be a hospital (also known as a facility), a clinic, or a doctor's office.

The term "healthcare provider visit" or just "visit" means a unique patient visit to a healthcare provider. During the actual visit, a set of services are provided to the patient for fees. These fees are determined by many different factors including, the free market, the provider, the location of the provider, the doctor, the patient diagnoses, the line of business of the care (e.g. inpatient, outpatient, emergency, etc.), the length of hospital stay, whether care was provided, and most importantly, the insurance that the patient is using for the visit since there are pre-negotiated rates and discounts between the provider and the insurance company. The data capture of a new visit for analysis purposes may start in advance of the first date of service for the visit as many providers use a combination of scheduling and pre-registration processes. Typically, the data elements captured include, but is not limited to the patient demographic information, date of the appointment, provider information, insurance information if the patient is insured, diagnostic information, and medical procedure information.

The term "alert" is the data representation of an issue in the data that needs to be brought to the attention of a user or an automated process in order to correct the issue. Individual alerts are configurable and are detected in the analytical processing of the data by either business or knowledge rules. Business rules are configured process steps that operate on the data while knowledge rules are simple Boolean expressions. The actual definition of an individual alert is based upon defined business processes within the healthcare provider organization.

As used herein, the terms "comprises", "comprising", "includes", "including", "has", "having", or any other variation thereof, are intended to cover a non-exclusive inclusion. For example, a method comprising a list of elements contains those elements but is not necessarily limited to those elements and may contain other elements not listed. Further, unless expressly stated to the contrary, "or" refers to an inclusive or and not to an exclusive or. For example, a condition A or B equals true if A is true (or present) and B is false (or not present), A is false (or not present) and B is true (or present), and both A and B are true (or present).

Attention is now directed to statistical financial systems and methods to value patient visits to healthcare provider organizations for follow up prioritization. These systems and methods may be used to first create a data model based on existing historical claims and visit data from a healthcare provider. Further, these systems and methods can be used to compare real-time visit data, either from an active patient or a scheduled visit in the future to the previously built model in order to create a value that can be assigned to both the visit and any resulting issues that are detected within the data after a series of rules evaluations. Furthermore, said value can be used a part of a prioritization scheme to have a user work on the most important issues for the provider from a financial perspective. This is because the items that have a greater financial impact will tend to be the items with heavier weights and this greater priority.

Figure 1:
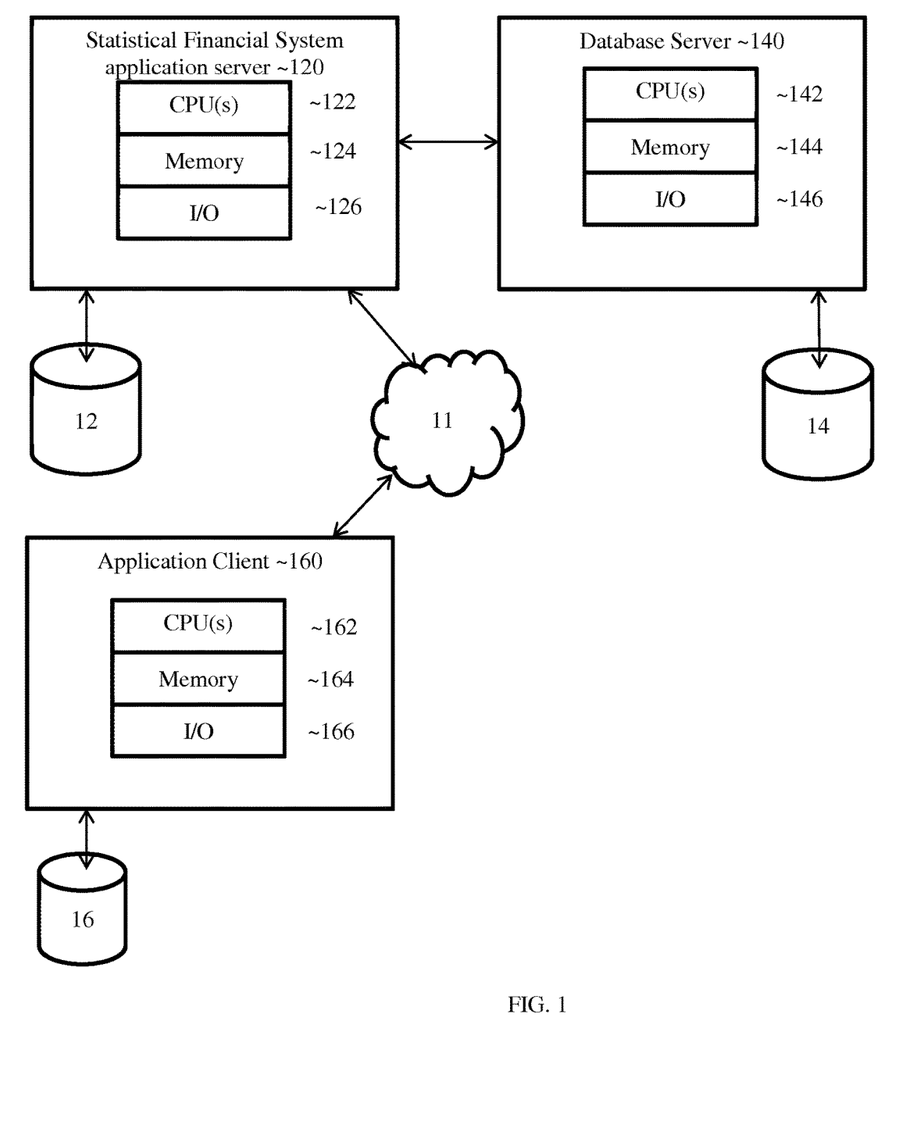
FIG. 1 includes an illustration of a hardware and network configuration of a statistical healthcare financial system and method in accordance with a specific, non-limiting embodiment.

Before discussing the embodiments of the invention defined by the appended claims, exemplary hardware architecture for using said embodiments is described. FIG. 1 illustrates an exemplary architecture where statistical financial system ("SFS") on computer 120, can be used to manage both statistical and structured healthcare data residing in database tables contained in database storage and managed by database server 140. SFS 120 can be bi-directionally attached to database server 140, which is attached to database storage 14. Database storage 14 may be direct or networked attached to database server 140. SFS 120 and Database Sever 140 may be part of a computer network. Note that FIG. 1 is a simplification of a hardware configuration.

Within SFS 120, a plurality of computers (not shown) may be interconnected to each other via a computer network. The computer on which SFS 120 may execute can include a plurality of central processing units (CPU) 122, memory 124, and Input/Output (I/O) 126. I/O 126 may include internal data buses, network cards, a keyboard, monitor, pointing devices, and storage and peripheral cards among others. The computer can be attached to a plurality of storage devices 12 either directly or via a network attached drive array, such as a storage area network (SAN).

The application client 160, is utilized by a user to interface with the application containing SFS 120. As diagrammed, the application client 160 connects to the SFS 120 through an interconnected network 11. This interconnected computer network 11 may be a local network or the public internet and may run the TCP/IP protocol or other protocols. In an alternate embodiment, the application client 160 may reside on the same local network as SFS 120, or even within the same computer. There may be a plurality of application clients 160 connected to the SFS 120 server over a network. The computer on which application client 160 may execute can include a plurality of central processing units (CPU) 162, memory 164, and Input/Output (I/O) 166. I/O 166 may include internal data buses, network cards, a keyboard, monitor, pointing devices, and storage and peripheral cards among others. The computer may be attached to a plurality of storage devices 16 either directly or via a network attached drive array, such as a storage area network (SAN).

Portions of the systems and methods described herein may be implemented in suitable software code that may reside within memory 124, memory 162, CPU 122, CPU 162, or storage devices 12,14, or 16. In addition, the instructions in an embodiment of said systems and methods may be contained on a data storage device with a different machine readable storage medium such as a hard disk drive.

Alternatively, the instructions may be stored as software code elements on a disk array, magnetic tape, diskette, CD ROM, DVD, optical storage device, or other appropriate machine readable medium or storage device.

In an illustrative embodiment of the systems and methods described herein, the machine-executable instructions may be lines of interpreted or compiled Java or other language code. In another illustrative embodiment of said systems and methods, the machine-executable instructions may be rules or simple expressions. Other architectures may be used. For examples, the functions of any of the systems and methods may be performed by different computers than are shown in FIG. 1. Additionally, a computer program or its software components with such code instructions may be embodied in more than one machine readable medium in more than one computer.

In the hardware configuration above, the various software components may reside on a single computer or on any combination of separate computers. In alternate embodiments, some or all of the software components may reside on the same computer.

Figure 2:
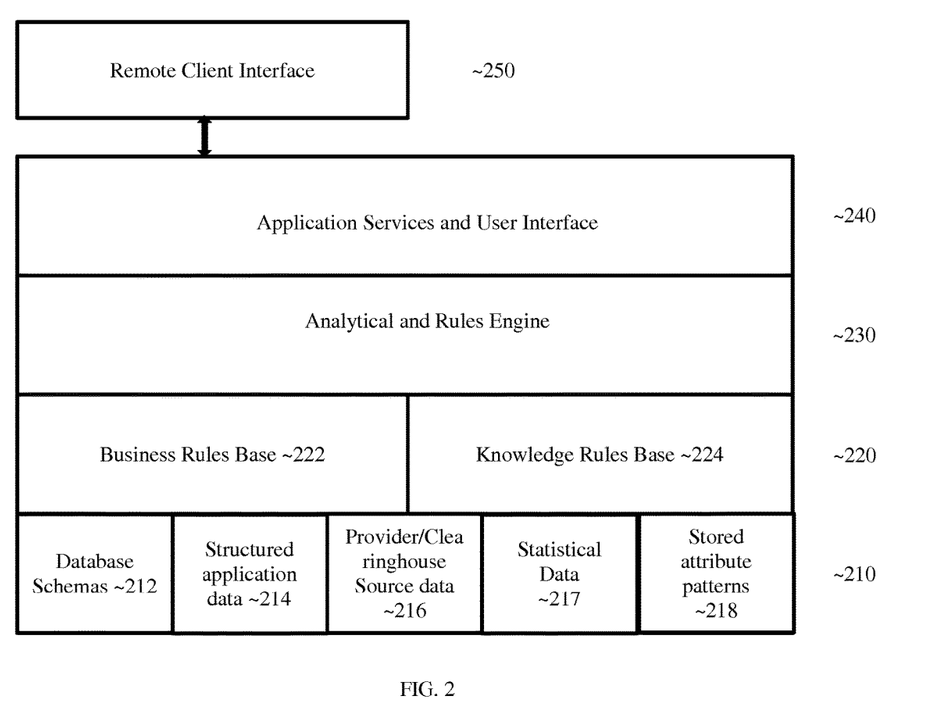
FIG. 2 is a representation of logical layers used in certain statistical healthcare financial systems.

Turning to FIG. 2, the logical layers of a typical statistical financial system for healthcare providers are represented. The lowest layer labeled 210 encompasses the basic persistence layer of the system. The database schemas 212 contain the fundamental data model upon which the application is based and defines tables, relationships between tables, primary and foreign keys, indexes, and data types. The healthcare data is structured and stored in as structured application data 214. The structured application data 214 includes all data necessary for the system to operate and for the methods to be performed. This data 214 includes relational and non-relational table data, XML and other marked up documents, text, object, expressions, rules, and process state data. The system operates on input data from healthcare providers and other sources, represented as Provider/Clearinghouse source data 216. This data may include ANSI ASC X12 data (837, 835, 270, 271, 276, 277, 278, etc), Health Level 7 (HL7 data), delimited text, XML or other machine readable formats. Once a sample of historical data is processed and analyzed for statistical patterns, it is stored as statistical data 217 for use in other parts of processing. The system will utilize the statistical data store 217 to create stored attribute patterns 218 to compare incoming visit data against in order to calculate value data.

The persistence layer contained within layer 210 and within a preferred embodiment of the invention outlined in the attached claims contains machine readable and executable instructions in the form of complex business rules and simple expressions. The business rules 222 are executed within the analytical and rules engine 230. These business rules 232 provide a flexible and configurable way to augment the machine instructions from a compiled language such as Java, which also execute in the analytical and rules engine 230. The knowledge rules 234 are more basic logical expressions that a skilled user can add to make additional decisions that take into account variables within their unique environment.

The analytical and rules engine 230 contains the majority of the machine executable instructions that process the data inputs (defined in FIG. 3) and implements the methods to provide a statistical valuation of a visit, issue, or alert. In an embodiment of this system, an application services and user interface layer 240 provides a means for a user to interact with a remote client 250 to operate an application that incorporates healthcare visits and alerts and the valuations thereof. The remote client 250, which may be on the same server or a different computer or computers attached over a network is an application such as a web browser that connects to the application services and user interface layer 240 to provide user-facing graphical interfaces to a person.

Figure 3:
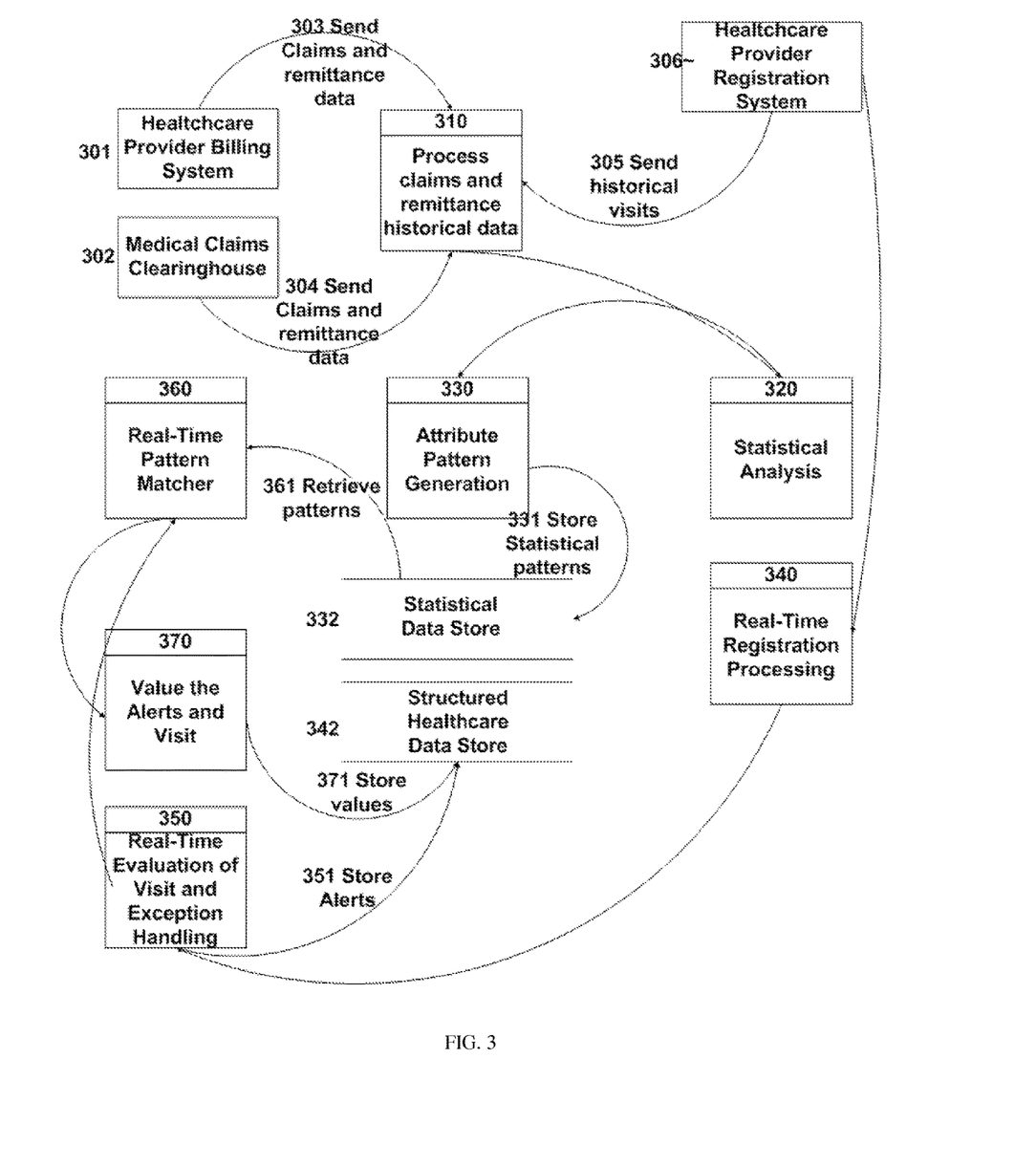
FIG. 3 is a data flow/process diagram of an embodiment of a statistical financial system and method to value patient visits to healthcare provider organizations for follow up prioritization.

Moving on to FIG. 3, The source data comprised of 303, 304, and 306 can come from multiple external systems including the healthcare provider billing system 301, the healthcare provider registration system 306, or a claims clearinghouse company 302. The data defined under 303 and 304 are typically ANSI ASC X12 837 and 835 files but may be print spool UB04/CMS1500 format other proprietary and custom text formats. The billing data (837, UB/CMS, or custom) contains informational elements such as the dates of service, insurance carrier, the insurance plan code, the facility where services were provided, total and line item charges, procedure codes (CPT4/HCPCS), diagnosis related group (DRG), diagnostic information, and physician information, amongst others. The remittance data (835 or custom) has matching information from the bill and includes the claim level and line item level payment, adjustment, reason code, and remark code information. In addition to billing and remittance data, there may be visit data associated with the patient registration. Typically, this is transmitted (but is not limited to) in a Health Level 7 (HL7) format and contains patient information, the service location, and insurance information, in addition to other information.

The aforementioned external data is loaded and processed by the historical claims and remittance module 310. A block of historical data, for example the data from the previous year, is parsed and split up into relational tables. The historical data is then fed into the statistical analysis module 320, which creates the attribute patterns 330. The statistical modeling starts with the identification of the independent variables used in the analysis. Based on the already mentioned data inputs, an exemplary set of independent variables are comprised of the insurance carrier, plan code, facility, service code, procedure code, primary diagnosis code, physician, and service location. The independent variables are used to predict the dependent variables, which are the allowed amount, contractual rate, coinsurance rate, total charges, and total payments. In the statistical analysis 320 using a large (historical) data set, the independent variables are selected based on their predictive power. Since the outcomes of a full historical set are known, the greater predictive power is where the difference between the predicted value and the real value have the best Sharpe ratio, minimum, standard deviation, and the an average approaching zero.

The independent variables are discrete variables and using bivariate analysis, the statistical analysis 320 creates statistical markers for the dependent variable, which are comprised of the n (sample size), q1 (value that is at the $25^{th}$ percentile of the matching attribute patterns), median, q3 (value that is at the $75^{th}$ percentile of the matching attribute patterns), min (minimum value of the matching attribute patterns), max (maximum value of the matching attribute patterns), sum (sum of the all of the values of the matching attribute patterns), and sum2 (sum of the squares of the values of the matching attribute patterns). The variables n, sum, and sum2 allow for many statistical calculations such as variance, standard deviation, and skew. All possible combinations of independent variables are calculated to obtain the marker for each of the dependent variables. The independent variables are also weighted based on their contribution to the prediction. The attribute pattern generation 320 saves a data representation of the known set of independent variables (attribute patterns) in order to obtain a fast query when needed later in the process. The result set of the fast query is analyzed to find the match that has the most significant statistical quality based on the target valuation desired. This attribute pattern set for fast query is stored in the statistical database 342.

Once the system has been tuned with historical data, the real time valuation process can begin. The historical tuning can be repeated over time. The valuation process starts as a new visit comes in from the healthcare registration system 306 and is processed by the real time registration processor 340, which takes the inbound visit data format, parses it, and hands it off to the real time evaluation of the visit and exception handling 350. This module stores a data representation of the visit and all of its attributes in the data store 342. Using a configurable set of rules and expressions, the visit is analyzed for any errors or issues. If errors or issues are detected an alert is raised and associated with the visit. Alerts are stored 351 in the data store 342.

After the visit attributes are determined, and any alerts are raised, the real time pattern matcher 360 creates the valuation of the visit and the alerts. Each visit has a known set of independent variables. Using this set, the fast query of an attribute pattern defined by 330 and stored in 332 is queried. The query forms a result set of aggregation values and this result set is ordered by the quality of the sample size, standard deviation, average value and the weighted value of each independent variable. Once the ordering is complete, the results are evaluated for the markers whereas the best predictive values are chosen and the target predictive value for each dependent variable. There are several valuation scenarios that may occur;
  1. Value of the entire visit—The predictive dependent variable for a valuation of a visit is the total payments. Among the independent variables selected, the insurance carrier, plan code, and procedure code are required. The attribute pattern with greatest sample size and least standard deviation is chosen.
  2. Value of the alert—The value is obtained for the entire visit. The value is then apportioned between the various open alerts based on the number of alerts, type of alert, and the configured weight of the alert.

In addition to the examples above, there are several variations that can occur; the value of an underpayment and the insured patient responsibility can be determined based on the dependent variable allowed amount. The value of the uninsured patient payment can be determined based on the dependent variable total charges.

Figure 4:
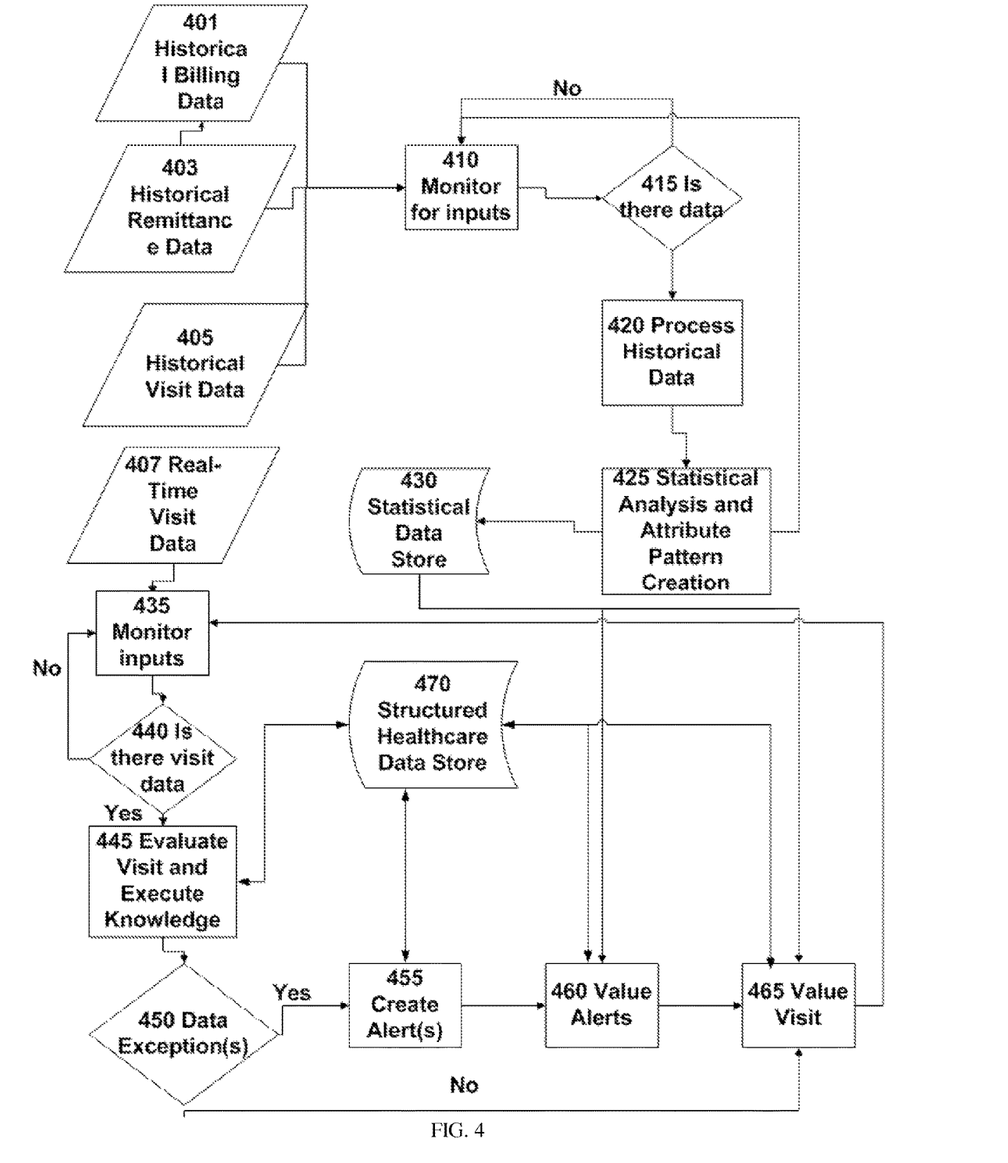
FIG. 4 includes a flowchart diagram of a statistical financial system and method to value patient visits to healthcare provider organizations for follow up prioritization in accordance with an embodiment of the said system and method.

Finally, turning to FIG. 4, the basic process flow is depicted. A process 410 monitors for inputs 401, 402, and 403, which contains the historical visit, billing, and remittance data. If data exists 415, then the process 420 loads the historical data, parses it, and breaks it up into individual data elements. If there is no data, the process 410 continues to monitor for changes.

After process 420 loads the data, process step 425 does the statistical analysis described previously during the description of FIG. 3. As previously describes, the best independent variables are selected. These variables are comprised of insurance carrier, plan code, facility, service code, procedure code, primary diagnosis code, physician, and service location. These independent variables are used to predict the dependent variables allowed amount, contractual rate, coinsurance rate, total charges, and total payments. Based on the desired outcome, the best variables are aggregated into an attribute pattern that can be matched later when new registrations are received. The attribute patterns are saved to the statistical data store 430 in either a high performance Berkeley file structure or a relational database table.

The process 435 monitors for real time inputs from 407. These inputs are received as patient events occur. These events comprise scheduling, pre-registration, registration, update, check-in, and discharge. If there is data 440, the process step 445 reads the data, breaks it apart, and analyzes it against a set of rules and expressions. The data representation of the visit processing is stored in data store 470 as relational information. If there is no data, the process step at 435 continues to monitor for new data.

The rules and expressions in 445 may detect issues and errors in the data and the decision point 450 evaluates if there are alerts that need to be raised. If there are alerts, the process step 455 creates the necessary alerts associated with the visit object and stores these alerts in the data store 470. Control is then passes to the Value Alerts step 460. In this step, the attribute pattern with greatest sample size and least standard deviation is chosen. As previously described in the description of FIG. 3, the value of the alerts are derived from the overall value obtained for the visit, which is then apportioned between the various open alerts based on the number of alerts, type of alert, and the configured weight of the alert. The results are stored in data store 470. Finally, the overall valuation of the visit is assigned. This is based on the attribute pattern with greatest sample size and least standard deviation and the result is stored in the data store 470. The outer process loop will return control to the input monitor 435 to start the process anew. In decision 450, if there are no alerts, then just the value of the visit is created in step 465 and stored in data store 470.

What is claimed is:

1. Within a computing architecture that includes a computer system comprising at least one processor, a computer-implemented method for operating the computing architecture in order to improve how healthcare services are managed and provisioned by facilitating generation and selective invocation of an optimized fast query that is generated using an attribute pattern derived from previously aggregated healthcare service data and that is used to provide high performance statistical analysis when evaluating new healthcare service data, the method comprising:
  instantiating an interface layer that provides an interface for a user to interact with a remote client, including accessing, via the remote client, one or more portions of healthcare provider data associated with a healthcare provider visit, the healthcare provider data including at least one previously generated attribute pattern associated with one or more past healthcare provider visits, the healthcare provider visit comprising a combination of professional services and healthcare items that are to be provided to a patient at the healthcare provider visit, each professional service and healthcare item having an associated monetary value;
  determining an attribute pattern that includes one or more visit-related variables associated with the professional services and healthcare items that are to be provided as part of the healthcare provider visit, wherein:
    the visit-related variables comprise a selected subset of independent and dependent variables used when calculating a value for the current healthcare provider visit based on one or more historical healthcare provider visits,
    the independent variables are selected based on their predictive power according to the at least one previously generated attribute pattern, a higher predictive power is manifest where a difference between a predicted monetary value and a real monetary value has an optimal Sharpe ratio, a minimum standard deviation, and an average approaching zero, the attribute pattern is determined according to one or more rules executed within an analytical and rules engine that provides a configurable way to augment machine instructions from a compiled language, the analytical and rules engine being configured to take into account environment-specific variables that influence the attribute pattern determination, the machine instructions are executed in the analytical and rules engine along with the one or more rules; and a data representation of the attribute pattern is stored in memory of the computer system;

after the attribute pattern is determined, generating a fast query that is optimized to specifically perform one or more attribute pattern queries on the determined attribute pattern, the optimized fast query being structured so that, when executed, it produces a result set that is used to subsequently identify a match between one or more previously generated attribute patterns and the determined attribute pattern, and wherein for the match to be identified based on the fast query's result set, a relationship between the one or more previously generated attribute patterns and the determined attribute pattern is required to satisfy a designated statistical quality level;

after generating the result set by executing the optimized fast query on the data representation of the attribute pattern such that the data representation stored in the computer system's memory is accessed during execution of the optimized fast query, using the result set to identify the match by comparing the healthcare provider data associated with the healthcare provider visit including the at least one previously generated attribute pattern to the determined attribute pattern to match the at least one previously generated attribute pattern with the newly determined attribute pattern in order to assign a monetary value, a weight, or a priority to the healthcare provider visit; and based on the comparison of the healthcare provider data to the determined attribute pattern, and prior to the healthcare provider visit taking place, calculating a predicted monetary value, a weight or a priority for the healthcare provider visit, the predicted monetary value, weight or priority indicating the order in which follow-up tasks performed after the healthcare provider visit are to be carried out for the healthcare provider visit.

2. The method of claim 1, wherein the monetary value, weight value, and priority are assigned to an alert or other detected issue with visit data.

3. The method of claim 1 where historical data is ANSI ASC X12 format.

4. The method of claim 1 where historical data is Health Level Seven (HL7 data), Clinical Context Object Workgroup ("CCOW"), or other text-based data from a Healthcare Information, Management, Billing, Scheduling, or Registration system.

5. The method of claim 1, wherein the said attribute patterns are derived from a plurality of tuples with combinations of attributes matching associated statistical variable results comprising average, mean, maximum, minimum, mode, median, quartiles, standard deviation, variance, standard error, skew and sample size for charges, contractual discount rates, net payments, copay, and coinsurance.

6. The method of claim 1, wherein a data input includes a plurality of attributes for said healthcare visit and its services comprising payer, payer plan, employer group, hospital name, department, hospital service, services name, diagnostics, primary and other procedures, individual procedures, patient sex, patient age, and physician name, and physician location.

7. The method of claim 6 wherein said data input is provided by an interface.

8. The method of claim 6 wherein said statistical variable results are processed by a plurality of custom knowledge rules wherein said knowledge rules are comprised of simple expressions and wherein said knowledge rules reduce the plurality of results to a single monetary value, weight value, or priority for the healthcare visit or alert or both.

9. The method of claim 8 wherein the result of said knowledge rule evaluation results in the execution of a custom extension to the process.

10. The method of claim 1 wherein the monetary value, weight value, or priority of a healthcare visit or alert or both are provided as input to a system with the purpose of aiding a user of said system in performing some follow-up task related to the underlying issue in said data or with the notification therein of said alerts and issues.

11. The method of claim 1, further comprising:
determining that the healthcare provider visit has been assigned a monetary value; and
associating the monetary value to one or more business rules to create a value processing weight for financial clearance decision making or prioritization of follow up tasks.

12. The method of claim 1, further comprising prioritizing follow-up tasks for those healthcare provider visits determined to be of highest monetary value.

13. A hardware storage device operating within a computing architecture that includes at least one processor and the hardware storage device, wherein the hardware storage device includes code embodied therein, the code, when executed by the at least one processor causes the computing architecture to improve how healthcare services are managed and provisioned by facilitating generation and selective invocation of an optimized fast query that is generated using an attribute pattern derived from previously aggregated healthcare service data and that is used to provide high performance statistical analysis when evaluating new healthcare service data, the code comprising:

an instruction for reading historical healthcare visit data associated with one or more healthcare provider visits, the healthcare provider data including at least one previously generated attribute pattern associated with one or more past healthcare provider visits, each healthcare provider visit comprising a combination of professional services and healthcare items that are to be provided to a patient at the healthcare provider visit, each professional service and healthcare item having an associated monetary value;

an instruction for performing a statistical analysis on the historical healthcare visit data;

an instruction for creation of attribute patterns using statistical variables, the attribute patterns comprising one or more visit-related variables associated with the professional services and healthcare items that are to be provided as part of the healthcare provider visit, wherein:

the visit-related variables comprise a selected subset of independent and dependent variables used when calculating a value for the current healthcare provider visit, the independent variables are selected based on their predictive power according to the at least one previously generated attribute pattern, a higher predictive power is manifest where the difference between a predicted monetary value and a real monetary value has an optimal Sharpe ratio, a minimum standard deviation, and an average approaching zero, the attribute pattern is determined according to one or more rules executed within an analytical and rules engine that provides a configurable way to augment machine instructions from a compiled language, the analytical and rules engine being configured to take into account environment-specific variables that influence the attribute pattern determination, the machine instructions are executed in the analytical and rules engine along with the one or more rules; and a data representation of the attribute pattern is stored in the hardware storage device;

an instruction for accepting healthcare data inputs including healthcare data inputs for at least one current healthcare visit;

an instruction for generating a fast query that is optimized to specifically perform one or more attribute pattern queries on the determined attribute pattern, the optimized fast query being structured so that, when executed, it produces a result set that is used to subsequently identify a match between one or more previously generated attribute patterns and the determined attribute pattern, and wherein for the match to be identified based on the fast query's result set, a relationship between the one or more previously generated attribute patterns and the determined attribute pattern is required to satisfy a designated statistical quality level, wherein the result set is generated by executing the optimized fast query on the data representation of the attribute pattern such that the data representation stored in the hardware storage device is accessed during execution of the optimized fast query;

an instruction to analyze said healthcare data inputs for data exceptions and issues;

an instruction to raise alerts on said data exceptions;

an instruction to use the result set to identify the match by comparing said healthcare data inputs including the at least one previously generated attribute pattern against said attribute patterns resulting in an assignment of a predicted monetary value, a weight, or a priority to said healthcare visits including the healthcare visit, or to the alerts, or to both, the weight or priority indicating the order in which follow-up tasks performed after the healthcare provider visit are to be carried out for the healthcare provider visit.

14. The computer-readable storage medium of claim 13, wherein the historical data is comprised of ANSI ASC X12 data, Health Level Seven (HL7 data), Clinical Context Object Workgroup ("CCOW"), or other text-based data from a Healthcare Information, Management, Billing, Scheduling, or Registration system.

15. The computer-readable storage medium of claim 13, wherein at least one of the instructions provides statistical attribute patterns comprising average, mean, maximum, minimum, mode, median, quartiles, standard deviation, variance, standard error, skew and sample size for charges, contractual discount rates, net payments, copay, and coinsurance.

16. The computer-readable storage medium of claim 13, wherein at least one of the instructions analyzes attributes for said healthcare visit and its services comprising payer, payer plan, employer group, hospital name, department, hospital service, services name, diagnostics, primary and other procedures, individual procedures, patient sex, patient age, and physician name, and physician location.

17. The computer-readable storage medium of claim 13, wherein at least one of the instructions is comprised of rules and simple expressions.

18. The computer-readable storage medium of claim 13, wherein at least one of the instructions uses the said assigned monetary value, weight, or priority of said visit, alert, or both to notify a user or to effect some follow-up task by a user for said alert.

19. The computer-readable storage medium of claim 13, wherein at least one of the instructions comprises a graphical user interface in conjunction with said visit or alert or both.

20. A computer system comprising the following:

one or more processors; and one or more computer-readable storage media having stored thereon computer-executable instructions that are executable by the one or more processors to cause the computer system to improve how healthcare services are managed and provisioned by facilitating generation and selective invocation of an optimized fast query that is generated using an attribute pattern derived from previously aggregated healthcare service data and that is used to provide high performance statistical analysis when evaluating new healthcare service data by causing the computer system to:

instantiate an interface layer that provides an interface for a user to interact with a remote client, including accessing, via the remote client, one or more portions of healthcare provider data associated with a healthcare provider visit, the healthcare provider data including at least one previously generated attribute pattern associated with one or more past healthcare provider visits, the healthcare provider visit comprising a combination of professional services and healthcare items that are to be provided to a patient at the healthcare provider visit, each professional service and healthcare item having an associated monetary value;

determine an attribute pattern that includes one or more visit-related variables associated with the professional services and healthcare items that are to be provided as part of the healthcare provider visit, wherein:

the visit-related variables comprise a selected subset of independent and dependent variables used when calculating a value for the current healthcare provider visit based on one or more historical healthcare provider visits, the independent variables are selected based on their predictive power according to the at least one previously generated attribute pattern, a higher predictive power is manifest where a difference between a predicted monetary value and a real monetary value has an optimal Sharpe ratio, a minimum standard deviation, and an average approaching zero, the attribute pattern is determined according to one or more rules executed within an analytical and rules engine that provides a configurable way to augment machine instructions from a compiled language, the analytical and rules engine being configured to take into account environment-specific variables that influence the attribute pattern determination, the machine instructions are executed in the analytical and rules engine along with the one or more rules; and a data representation of the attribute pattern is stored in the computer system's one or more computer-readable storage media;

after the attribute pattern is determined, generate a fast query that is optimized to specifically perform one or more attribute pattern queries on the determined attribute pattern, the optimized fast query being structured so that, when executed, it produces a result set that is used to subsequently identify a match between one or more previously generated attribute patterns and the determined attribute pattern, and wherein for the match to be identified based on the fast query's result set, a relationship between the one or more previously generated attribute patterns and the determined attribute pattern is required to satisfy a designated statistical quality level;

after generating the result set by executing the optimized fast query on the data representation of the attribute pattern such that the data representation stored in the computer system's one or more computer-readable storage media is accessed during execution of the optimized fast query, use the result set to identify the match by comparing the healthcare provider data associated with the healthcare provider visit including the at least one previously generated attribute pattern to the determined attribute pattern to match the at least one previously generated attribute pattern with the newly determined attribute pattern in order to assign a monetary value, a weight, or a priority to the healthcare provider visit; and based on the comparison of the healthcare provider data to the determined attribute pattern, and prior to the healthcare provider visit taking place, calculate a predicted monetary value, a weight or a priority for the healthcare provider visit, the predicted monetary value, weight or priority indicating the order in which follow-up tasks performed after the healthcare provider visit are to be carried out for the healthcare provider visit.

\* \* \* \* \*